United States Patent
Shou et al.

(10) Patent No.: US 11,254,628 B1
(45) Date of Patent: Feb. 22, 2022

(54) METHODS OF BUTANE HYDROGENOLYSIS UNDER HYDROGEN-LEAN CONDITIONS

(71) Applicant: SABIC Global Technologies B.V., Bergen op Zoom (NL)

(72) Inventors: Heng Shou, Sugar Land, TX (US); Byeongjin Baek, Sugar Land, TX (US); Robert R. Broekhuis, Sugar Land, TX (US); Dustin Fickel, Sugar Land, TX (US); Istvan Lengyel, Sugar Land, TX (US); Emiel Van Kimmenade, Geleen (NL)

(73) Assignee: SABIC GLOBAL TECHNOLOGIES B.V., Bergen op Zoom (NL)

( * ) Notice: Subject to any disclaimer, the term of this patent is extended or adjusted under 35 U.S.C. 154(b) by 42 days.

(21) Appl. No.: 16/941,031

(22) Filed: Jul. 28, 2020

(51) Int. Cl.
   *C07C 4/06* (2006.01)
   *B01J 29/44* (2006.01)
   *C07C 5/22* (2006.01)

(52) U.S. Cl.
   CPC .............. *C07C 4/06* (2013.01); *B01J 29/44* (2013.01); *C07C 5/2206* (2013.01); *C07C 2523/42* (2013.01); *C07C 2523/46* (2013.01); *C07C 2529/44* (2013.01)

(58) Field of Classification Search
   CPC ..... C07C 4/06; C07C 5/2206; C07C 2529/44; C07C 2523/42; C07C 2523/46; B01J 29/44
   See application file for complete search history.

(56) References Cited

U.S. PATENT DOCUMENTS

| | | |
|---|---|---|
| 3,679,574 A | 7/1972 | Irvine |
| 3,708,420 A | 1/1973 | Irvine |
| 3,898,298 A | 8/1975 | Desiderio et al. |
| 4,061,690 A | 12/1977 | Bernard et al. |
| 4,140,621 A | 2/1979 | Franck et al. |
| 4,166,077 A | 8/1979 | Bernard et al. |

(Continued)

FOREIGN PATENT DOCUMENTS

| | | |
|---|---|---|
| WO | WO 2012/071137 | 5/2012 |
| WO | WO 2020/061010 | 3/2020 |

(Continued)

OTHER PUBLICATIONS

Hibbitts, et al., "Effects of Chain Length on the Mechanism and Rates of Metal-Catalyzed Hydrogenolysis of n-Alkanes." *The Journal of Physical Chemistry*, C(120):8125-8138, 2016.

(Continued)

*Primary Examiner* — Youngsul Jeong
*Assistant Examiner* — Jason Y Chong
(74) *Attorney, Agent, or Firm* — Norton Rose Fulbright US LLP

(57) ABSTRACT

Processes for the hydrogenolysis of butane are described. A process can include (a) introducing a butane feed and hydrogen to a first hydrogenolysis reactor comprising a hydrogenolysis catalyst, and (b) contacting the butane feed and hydrogen with the hydrogenolysis catalyst at conditions sufficient to produce a first hydrogenolysis product stream. The introduction of the butane feed stream and hydrogen to the first hydrogenolysis reactor can be controlled to maintain a hydrogen to butane molar ratio in the reactor inlet of 0.3:1 to 0.8:1.

15 Claims, 11 Drawing Sheets

(56) References Cited

U.S. PATENT DOCUMENTS 4,191,845 A * 3/1980 Rubin ...................... C07C 5/03
585/251
4,430,203 A 2/1984 Cash

FOREIGN PATENT DOCUMENTS

WO     WO 2020/061011     3/2020
WO     WO 2020/061012     3/2020

OTHER PUBLICATIONS

Hibbitts, et al., "Role of Branching on the Rate and Mechanism of C-C Cleavage in Alkanes on Metal Surfaces." *ACS Catalysis*, 6:469-482, 2015.
Kempling et al., "Hydrogenolysis of n-Butane on Supported Ruthenium." *Ind. Eng. Chem. Process. Des. Dev.*, 9:116-120, 1970.

* cited by examiner

METHODS OF BUTANE HYDROGENOLYSIS UNDER HYDROGEN-LEAN CONDITIONS

CROSS REFERENCE TO RELATED APPLICATIONS

None.

BACKGROUND OF THE INVENTION

A. Field of the Invention

The invention generally concerns processes for the hydrogenolysis of butane. A process can include controlling the introduction of a butane feed stream and hydrogen to a first hydrogenolysis reactor such that the hydrogen to butane molar ratio in the reactor is controlled from 0.3:1 to 0.8:1.

B. Description of Related Art

Butane is used extensively in petroleum refining and the chemical industry as part of the process to make natural gas, various fuels, distillates, naphtha, gasoline, gasoline additives, and other refined products such as plastics and catalysts. Butane isomers are also used in different processes as well as different products. Isobutane, which can be used as fuel, a refrigerant, a propellant, or used to produce isobutylene, has a higher value than n-butane, which can be used as fuel or to produce butene, propane, ethane, or methane.

Light alkanes can be obtained from a butane ($C_4$) stream through steam cracking, hydrocracking reactions, and/or through hydrogenolysis reactions. However, steam cracking of a butane feedstock produces relatively low yield of ethylene. Processes based on hydrocracking and/or hydrogenolysis reactions can produce a more favorable product composition. In some instances, hydrogenolysis reaction can be advantageous. However, known hydrogenolysis reactions suffer in that they generally cannot effectively convert isobutane to ethane. This is problematic as butane streams often include both n-butane and isobutane.

The hydrogenolysis of butanes is shown in reaction schemes (1)-(3):

$$n\text{-}C_4H_{10} + H_2 \rightarrow 2C_2H_6 \tag{1}$$

$$n\text{-}C_4H_{10} + H_2 \rightarrow C_3H_8 + CH_4 \tag{2}$$

$$i\text{-}C_4H_{10} + H_2 \rightarrow C_3H_8 + CH_4 \tag{3}$$

Reaction scheme 1 is the desired hydrogenolysis reaction, while reactions schemes 2 and 3 show the side reactions. Conditions used for butane hydrogenolysis can rapidly deactivate catalysts and to mitigate catalyst deactivation, conventional processes have increased the partial pressure of hydrogen provided to the reactor. However, excessive hydrogen can only provide marginal improvements in catalyst deactivation. Moreover, the addition of hydrogen can add substantial capital and operational cost for separating and recycling hydrogen. By way of example, U.S. Pat. No. 4,140,621 to Franck et al. describes hydrogenolysis of $C_4$ to $C_7$ feed to a product composition that includes ethane and propane. The process uses a preferred hydrogen to butane ratio being of 1 to 20. The highest amount of ethane was observed when a $H_2:C_4\text{-}C_7$ feed molar ratio of 6 was used. This process suffers, like many conventional operations, in that operating at hydrogen-rich conditions decreases the reaction rates, which can require an increase in the reactor size to achieve the desired production rate. Furthermore, a larger separation section could be needed for hydrogen recycling. Both can contribute to capital and operational costs.

While various attempts to produce $C_2$ hydrocarbons from $C_4$ hydrocarbons have been made, there is still improvement needed to mitigate catalyst deactivation and/or increase the cost efficiency of the process.

SUMMARY OF THE INVENTION

A solution to at least some of the problems associated with catalyst deactivation and/or cost inefficiencies during hydrogenolysis of butane has been discovered. At least one solution is focused on using less than stoichiometric amounts of hydrogen. In the present invention, a mole ratio of $H_2:C_4H_{10}$ of 0.8:1 or less at the reactor inlet is used. Preferably, the mole ratio is 0.3:1 to 0.8:1 and more preferably 0.5:1 to 0.8:1, most preferably 0.7:1 to 0.8:1, or about 0.75:1. This ratio, which is lean in hydrogen can provide for decreased capital expenditures for separation of the $H_2$ from the product composition. The use of less than stoichiometric amounts of hydrogen can also allow for the use of multiple reactors in series, which allows for inter-stage addition of hydrogen and provides the further advantage of mitigating catalyst deactivation, particularly when the $H_2:C_4H_{10}$ molar ratio of subsequent series reactors is controlled in the reactor inlet as further described below.

In some aspects of the present invention, processes for the hydrogenolysis of butane are described. A process can include (a) introducing a butane feed (e.g., a mixture of n-butane and isobutane) and hydrogen to a first hydrogenolysis reactor that includes a hydrogenolysis catalyst, and (b) contacting the butane feed and hydrogen with the hydrogenolysis catalyst at conditions sufficient to produce a first hydrogenolysis product stream. The introduction of the butane feed stream and hydrogen to the first hydrogenolysis reactor can be controlled to effect a hydrogen to butane molar ratio in the reactor inlet at 0.3:1 to 0.8:1, preferably 0.5:1 to 0.8:1. The n-butane can be present in the butane feed stream in an amount of equal to or greater than about 50 mol. % (e.g., 50 to 100 mol. %). It should be understood that the expression "controlled to effect a hydrogen to butane molar ratio in the reactor inlet" means that the feed stream is controlled such that hydrogen to butane molar ratio is within the recited ratio at at least one location in the reactor inlet. Reactor conditions can include a temperature of from about 245° C. to about 330° C., a pressure of from about 101 kPa (0 psig) to 1370 kPa (200 psig), and a butane feed-based weight hourly space velocity (WHSV) of from about 1 h$^{-1}$ to about 100 h$^{-1}$, (preferably 10 h$^{-1}$ to 90 h$^{-1}$) or combinations thereof. The hydrogenolysis catalyst can include (a) a bimetallic supported catalyst, (b) a monometallic supported catalyst, or (c) mixtures thereof. The bimetallic supported catalyst can include a support, a first catalytic metal, a second catalytic metal that is different than the first catalytic metal, and optionally binder. The monometallic supported catalyst can include a third catalytic metal, a support, and optionally binder. Non-limiting examples of the first metal, the second metal, and the third metal can include iridium (Ir), platinum (Pt), rhodium (Rh), ruthenium (Ru), rhenium (Re), palladium (Pd), molybdenum (Mo), tungsten (W), nickel (Ni), cobalt (Co), or any combination thereof. In a preferred aspect, the hydrogenolysis catalyst is a bimetallic catalyst that can include Ir and Pt. The support can include alumina, a zeolite, or both. The zeolite can be selected from ZSM-5, ZSM-11, Y, high-silica Y, USY, EU-1, EU-2, beta, L, ferrierite, CHA, SSZ-16, Nu-3, sigma-1, silicalite-1, and combinations thereof. The optionally binder can include alumina, titania, silica, or combinations thereof. A non-limiting example of the hydrogenolysis catalyst can include 0.3 wt. % Pt-0.3 wt. % Ir/γ-Al$_2$O$_3$-HZSM-5. The support of such a catalyst can include 80 wt. % H-ZSM-5 and 20 wt. % γ-Al$_2$O$_3$.

In some embodiments, the process includes feeding the first hydrogenolysis product stream to a separation unit and separating one or more components of the first hydrogenolysis product stream. A separated component of the one or more components can include a mixture of isobutane and n-butane. The method can include feeding the separated component comprising isobutane and n-butane to an isomerization unit and converting the isobutane to n-butane to produce a stream enriched in n-butane.

In other embodiments, the process can include recycling unconverted hydrogen and butane from the first hydrogenolysis product stream to the first hydrogenolysis reactor to increase conversion of the butane feed stream and hydrogen to the hydrogenolysis product stream. In yet another embodiment, the process can include feeding unconverted hydrogen and butane from the first hydrogenolysis product stream to one or more sequential hydrogenolysis reactors to increase conversion of the butane feed stream to the hydrogenolysis product stream.

In some aspects, the process can include feeding the hydrogenolysis product stream from the first hydrogenolysis reactor to one or more sequential hydrogenolysis reactors to form one or more sequential hydrolysis product streams to increase conversion of the butane feed stream in a final hydrogenolysis product stream. The first hydrogenolysis product stream and any one or more of the sequential hydrogenolysis product streams can be passed through a heat exchanger. The reactor inlet temperatures of the first hydrogenolysis reactor, and of the one or more sequential hydrogenolysis reactors, can be between 245° C. and 300° C., preferably 245° C. to 290° C. In some embodiments, the WHSV can be 1 h$^{-1}$ to 100 h$^{-1}$ with respect to the first reactor; and a butane-based WHSV of 1 h$^{-1}$ to 100 h$^{-1}$ with respect to the entire reactor series. In some embodiments, the temperature differential between the reactor inlet temperature and the reactor outlet temperature can be maintained between 20° C. to 50° C. or about 25° C. In some aspects, the process can include injecting additional hydrogen into one or more of the first hydrogenolysis product streams and the sequential hydrogenolysis reactors. The amount of additional injected hydrogen can be represented by the formula $R_{n+1}$ is $\geq R_n$ where $R_n$ represents the value for the molar ratio of hydrogen to butane in a n$^{th}$ reactor inlet and $R_{n+1}$ represents the molar ratio of hydrogen to butane in a reactor inlet sequential $R_n$.

In some embodiments, the process can include feeding the final hydrogenolysis product stream to a separation unit and separating one or more components of the final hydrogenolysis product stream. In some aspects, the process can include feeding a component that includes unreacted isobutane and n-butane to an isomerization unit and converting the isobutane to n-butane to produce a stream enriched in n-butane.

In one aspect of the present invention, 20 embodiments are described. Embodiment 1 describes a process for the hydrogenolysis of butane, the process comprising: (a) introducing a butane feed and hydrogen to a first hydrogenolysis reactor comprising a hydrogenolysis catalyst; and (b) contacting the butane feed and hydrogen with the hydrogenolysis catalyst at conditions sufficient to produce a first hydrogenolysis product stream, wherein the introduction of the butane feed stream and hydrogen to the first hydrogenolysis reactor is controlled to effect a hydrogen to butane molar ratio in the reactor inlet of 0.3:1 to 0.8:1. Embodiment 2 is the process of embodiment 1, wherein the hydrogen to butane molar ratio in the reactor inlet is 0.5:1 to 0.8:1. Embodiment 3 is the process of any one of embodiments 1 to 2, wherein the butane feed stream comprises n-butane and iso-butane and n-butane is present in the butane feed stream in an amount of equal to or greater than about 50 mol %. Embodiment 4 is the process of any one of embodiments 1 to 3, wherein the conditions comprise a temperature of 245° C. to about 330° C., a pressure of from about 101 kPa (0 psig) to about 2100 kPa (300 psig), and a butane-based weight hourly space velocity (WHSV) of 1 to about 100 or combinations thereof. Embodiment 5 is the process of any one of embodiments 1 to 4, wherein the hydrogenolysis catalyst comprises: (a) a bimetallic supported catalyst comprising a support, a first catalytic metal, a second catalytic metal, and optionally binder, wherein the first and second catalytic metals are different, (b) a monometallic supported catalyst, the monometallic catalyst comprising a third catalytic metal, a support, and optionally binder, or (c) mixtures of (a) and (b), wherein the first metal, the second metal, and the third metal each independently include iridium (Ir), platinum (Pt), rhodium (Rh), ruthenium (Ru), rhenium (Re), palladium (Pd), molybdenum (Mo), tungsten (W), nickel (Ni), or cobalt (Co), or any combination thereof. Embodiment 6 is the process of embodiment 5, wherein the hydrogenolysis catalyst comprises the bimetallic supported catalyst, which comprises Ir and Pt. Embodiment 7 is the process of any one of embodiments 5 to 6, wherein the support comprises alumina, a zeolite, or both, wherein the zeolite comprises ZSM-5, ZSM-11, Y, high-silica Y, USY, EU-1, EU-2, beta, L, ferrierite, CHA, SSZ-16, Nu-3, sigma-1, or silicalite-1, or any combination thereof, and wherein the optionally binder comprises alumina, titania, silica, or combinations thereof. Embodiment 8 is the process of embodiment 7, wherein the hydrogenolysis catalyst comprises 0.3 wt. % Pt-0.3 wt. % Ir/γ-Al$_2$O$_3$-HZSM-5. Embodiment 9 is the process of embodiment 8, wherein the support is 80 wt. % H-ZSM-5 and 20 wt. % γ-Al$_2$O$_3$. Embodiment 10 is the process of any one of embodiments 1 to 9, further comprising feeding the first hydrogenolysis product stream to a separation unit and separating one or more components of the first hydrogenolysis product stream. Embodiment 11 is the process of embodiment 10, wherein a separated component of the one or more components comprises isobutane and the method further comprises feeding the separated component comprising isobutane to an isomerization unit and converting the isobutane to n-butane to produce a stream enriched in n-butane. Embodiment 12 is the process of any one of embodiments 1 to 11, further comprising recycling unconverted hydrogen and n-butane from the first hydrogenolysis product stream to the first hydrogenolysis reactor to increase conversion of the n-butane feed stream and hydrogen. Embodiment 13 is the process of any one of embodiments 1 to 12, further comprising feeding unconverted hydrogen and butane feed from the first hydrogenolysis product stream to one or more sequential hydrogenolysis reactors to increase overall conversion of the butane feed stream to the hydrogenolysis product stream. Embodiment 14 is the process of any one of embodiments 1 to 13, further comprising feeding the hydrogenolysis product stream from the first hydrogenolysis reactor to one or more sequential hydrogenolysis reactors to form one or more sequential hydrolysis product streams to increase conversion of the butane feed stream in a final hydrogenolysis product stream.

Embodiment 15 is the process of embodiment 14, further comprising passing the first hydrogenolysis product stream and any one or more of the sequential hydrogenolysis product streams through a heat exchanger. Embodiment 16 is the process of any one of embodiments 1 to 15, wherein the reactor inlet temperatures of the first hydrogenolysis reactor, and of the one or more sequential hydrogenolysis reactors is between 240° C. and 300° C., preferably 245° C. to 290° C. Embodiment 17 is the process of embodiment 16, further comprising injecting additional hydrogen into one or more of the hydrogenolysis product streams and the sequential hydrogenolysis reactors. Embodiment 18 is the process of embodiment 17, further comprising selecting an amount of additional hydrogen based on $R_{n+1} \geq R_n$ where $R_n$ represents a molar ratio of hydrogen to butane in the reactor inlet of a $n^{th}$ reactor, and $R_{n+1}$ represents the molar ratio of hydrogen to butane in a reactor inlet sequential to $R_n$. Embodiment 19 is the process of embodiment 18, further comprising feeding the final hydrogenolysis product stream to a separation unit and separating one or more components of the final hydrogenolysis product stream. Embodiment 20 is the process of embodiment 19, further comprising feeding a component comprising unreacted isobutane, or an unreacted mixed butane stream, to an isomerization unit and converting the isobutane to n-butane to produce a stream enriched in n-butane.

Other embodiments of the invention are discussed throughout this application. Any embodiment discussed with respect to one aspect of the invention applies to other aspects of the invention as well and vice versa. Each embodiment described herein is understood to be embodiments of the invention that are applicable to other aspects of the invention. It is contemplated that any embodiment or aspect discussed herein can be combined with other embodiments or aspects discussed herein and/or implemented with respect to any method or composition of the invention, and vice versa. Furthermore, compositions of the invention can be used to achieve methods of the invention.

The following includes definitions of various terms and phrases used throughout this specification.

The phrase "reactor inlet" refers to the zone or space between the hydrogen injection inlet and the head of the catalyst bed. The measurement of $H_2$-to-$C_4H_{10}$ ratios can be determined by a person of engineering skill. For example, a direct measurement using an on-line GC analysis of the $H_2/C_4H_{10}$ mixture at any point(s) in the reactor inlet can be used to determine the $H_2$-to-$C_4H_{10}$ molar ratio in the $H_2/C_4H_{10}$ mixture. Other methodology for determining the $H_2$-to-$C_4H_{10}$ molar ratio can include indirect measurement such as a combination of a kinetic model and mass flowmeters readouts of the feeds (hydrogen and butane feeds) entering the reactor inlet. If more than one sample of the $H_2/C_4H_{10}$ mixture is used, an average value of the samples can be used to determine the $H_2$-to-$C_4H_{10}$ molar ratio in the $H_2/C_4H_{10}$ mixture.

The terms "about" or "approximately" are defined as being close to as understood by one of ordinary skill in the art. In one non-limiting embodiment, the terms are defined to be within 10%, preferably within 5%, more preferably within 1%, and most preferably within 0.5%.

The terms "wt. %," "vol. %," or "mol. %" refers to a weight percentage of a component, a volume percentage of a component, or molar percentage of a component, respectively, based on the total weight, the total volume of material, or total moles, that includes the component. In a non-limiting example, 10 grams of component in 100 grams of the material is 10 wt. % of component.

The term "substantially" and its variations are defined to include ranges within 10%, within 5%, within 1%, or within 0.5%.

The terms "inhibiting" or "reducing" or "preventing" or "avoiding" or any variation of these terms, when used in the claims and/or the specification includes any measurable decrease or complete inhibition to achieve a desired result.

The term "effective," as that term is used in the specification and/or embodiments, means adequate to accomplish a desired, expected, or intended result.

The use of the words "a" or "an" when used in conjunction with any of the terms "comprising," "including," "containing," or "having" in the claims, or the specification, may mean "one," but it is also consistent with the meaning of "one or more," "at least one," and "one or more than one."

The words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The processes of the present invention can "comprise," "consist essentially of," or "consist of" particular ingredients, components, compositions, etc. disclosed throughout the specification. With respect to the transitional phrase "consisting essentially of," in one non-limiting aspect, a basic and novel characteristic of the processes of the present invention is their ability to use less than stoichiometric amounts of hydrogen for butane hydrogenolysis reactions.

Other objects, features and advantages of the present invention will become apparent from the following figures, detailed description, and examples. It should be understood, however, that the figures, detailed description, and examples, while indicating specific embodiments of the invention, are given by way of illustration only and are not meant to be limiting. Additionally, it is contemplated that changes and modifications within the spirit and scope of the invention will become apparent to those skilled in the art from this detailed description. In further embodiments, features from specific embodiments may be combined with features from other embodiments. For example, features from one embodiment may be combined with features from any of the other embodiments. In further embodiments, additional features may be added to the specific embodiments described herein.

BRIEF DESCRIPTION OF THE DRAWINGS

Advantages of the present invention may become apparent to those skilled in the art with the benefit of the following detailed description and upon reference to the accompanying drawings.

FIG. 9A illustrates n-butane conversion; FIG. 9B illustrates isobutane conversion. FIG. 9C illustrates ethane selectivity. FIG. 9D illustrate temperature. FIG. 9E illustrates catalyst activity after 1000 hours. Case 1: no extra hydrogen was added. Case 2 extra $H_2$ via inter-stage addition. Case 3 all extra $H_2$ upfront. Reaction conditions were the same in three cases and were feed: 70% n-butane and 30% i-butane, WHSV=4 $h^{-1}$ (with respect to the entire reactor series), $p_{inlet}$=8.6 bar, $p_{outlet}$=7.9 bar, catalyst: 0.3 wt. % Pt-0.3 wt. % Ir/γ-$Al_2O_3$—H-ZSM-5, ΔT=40° C. (per reactor).

FIG. 10A is ethane selectivity for the two cases. FIG. 10B is catalyst activity after 1000 hours. Reaction conditions were: feed: 70% n-butane and 30% i-butane, WHSV=4 $h^{-1}$ (with respect to the entire reactor series), $p_{inlet}$=8.6 bar, $p_{outlet}$=7.9 bar, catalyst: 0.3 wt. % Pt-0.3 wt. % Ir/γ-$Al_2O_3$—H-ZSM-5, ΔT=40° C. (per reactor).

Figure 1:
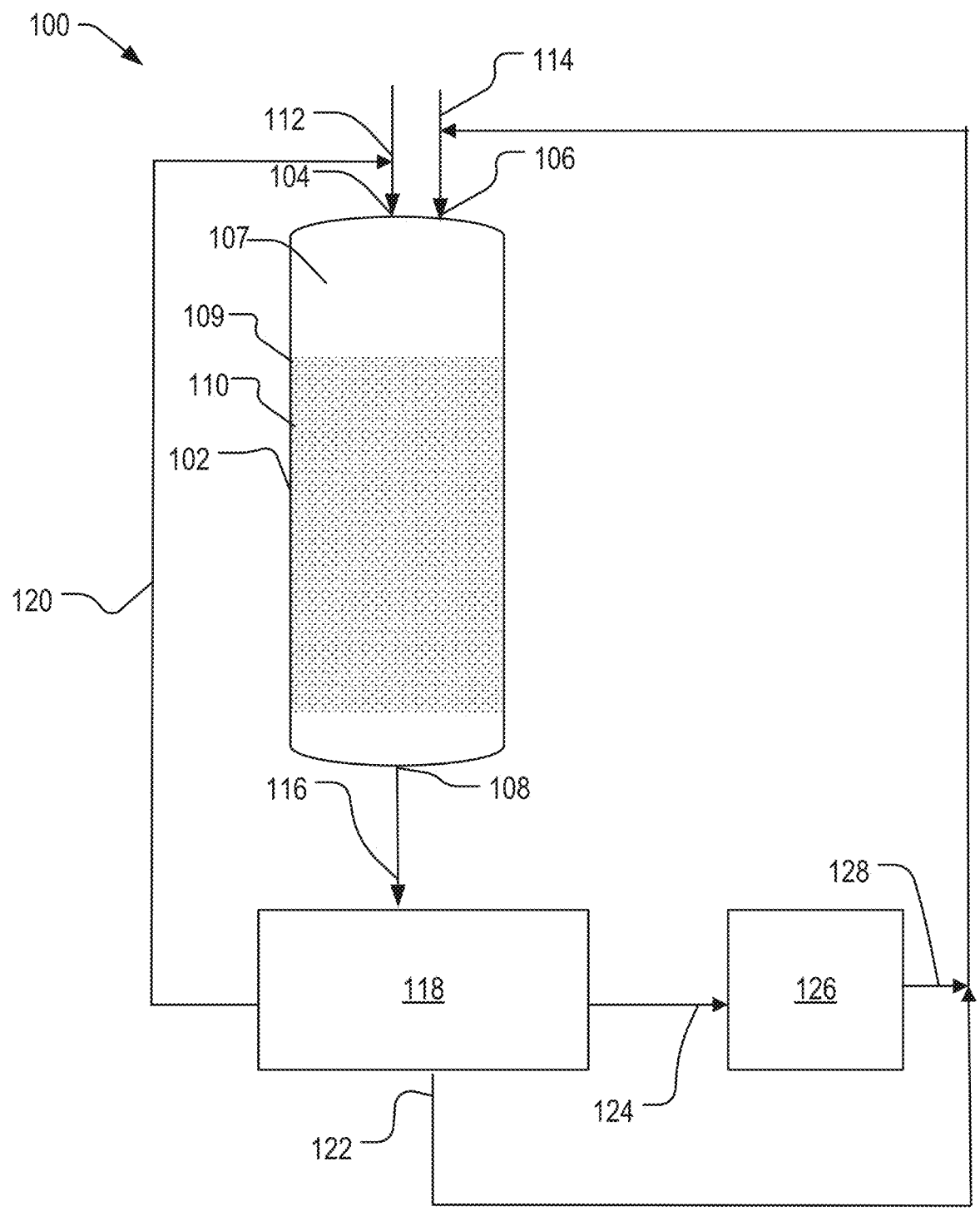
FIG. 1 is an illustration of the process of the present invention using one reactor.

While the invention is susceptible to various modifications and alternative forms, specific embodiments thereof are shown by way of example in the drawings. The drawings may not be to scale.

DETAILED DESCRIPTION OF THE INVENTION

A solution to at least some of the problems associated with the hydrogenolysis of butane reaction has been discovered. In one aspect, the solution can include maintaining the $H_2$:$C_4H_{10}$ molar ratio to stoichiometric or less than stoichiometric amounts. It has been discovered that a $H_2$:$C_4H_{10}$ molar ratio in the range of 0.3:1 to 0.8:1, preferably 0.5:1 to 0.8:1, provides the least amount of catalyst deactivation as compared to $H_2$:$C_4H_{10}$ molar ratios greater than 0.8:1. As shown in a non-limiting manner in the Examples, when the $H_2$:$C_4H_{10}$ molar ratios are less than 0.3 and greater than 0.99 at the reactor inlet of the first reactor the activity of the catalyst diminishes. In contrast, as shown in a non-limiting manner in the Examples when the molar ratio is between 0.3:1 and 0.8:1, preferably 0.5:1 to 0.8:1, more preferably 0.7:1 to 0.8:1, most preferably about 0.75:1, at the reactor inlet, the catalyst lifetime was about 20% longer after 1000 hours than when the ratios is outside of the 0.3 to 0.8 range.

These and other non-limiting aspects of the present invention are discussed in further detail in the following sections with reference to the figures.

A. Butane Hydrogenolysis Process and Systems

FIG. 1 depicts a schematic for a process for the hydrogenolysis of butane with one reactor. FIGS. 2-6 depict schematic for butane hydrogenolysis using multiple reactors, separation units, and isomerization units. Reactor system 100 a reactor 102 (e.g., a fixed-bed reactor), an inlet 104 for a $H_2$ reactant feed, an inlet 106 for a butane reactant feed, and an outlet 108 configured to remove a hydrogenolysis product stream from the reaction zone. The reactor 102 can include hydrogenolysis catalyst bed 110. $H_2$ reactant feed 112 can enter the reactor 102 via the $H_2$ inlet 104. Butane feed 114 can be a mixture of butanes (e.g., isobutane and n-butane) and enter reactor 102 via butane inlet 106. $H_2$ and butane feeds mix in reactor inlet 107 to produce desired a $H_2$/butane ratio that contacts catalyst bed 110. Reactor inlet 107 can be the zone or space between the top 109 of catalyst bed 110 and $H_2$ inlet 104 positioned upstream of the catalyst bed. The measurement of $H_2$-to-$C_4H_{10}$ ratios in reactor inlet 107 can be determined by a person of engineering skill. For example, a direct on-line GC analysis in the reactor inlet 107 can be used to determine the $H_2/C_4H_{10}$ mole ratio in the $H_2/C_4H_{10}$ mixture in reactor inlet 107. The in-line GC sample port is positioned downstream of the hydrogen and butane inlets, for example, but not limited to, in a middle section of the reactor inlet. In another example, mass flowmeters can be coupled to $H_2$ inlet 104 and $C_4H_{10}$ inlet 106 to regulate and/or monitor the amount of $H_2$ and $C_4H_{10}$ entering reactor inlet 107. The data from the mass flow meters can be used in combination with a kinetic model to determine the mole ratio of $H_2/C_4H_{10}$ in reactor inlet 107. In some embodiments, the $H_2$ reactant feed and/or the butane reactant feed can be used to maintain a pressure in the reactor 102. Reactor 102 can include one or more catalysts beds. In some embodiments, the reactant feed streams include inert gas (e.g., nitrogen or argon). In some embodiments, the reactant feeds are provided at the same timer or in reverse order. In some embodiments, only one reactant feed is used. Contact of the reactant feed streams 112 and 114 with the hydrogenolysis catalyst produce hydrogenolysis product stream 116, which includes ethane, methane, and propane as hydrogenolysis products. After a sufficient amount of time, hydrogenolysis product stream 116 can be removed from the reactor 102 via product outlet 108. Hydrogenolysis product stream 116 can be sent to other processing units (e.g., separation units, isomerization units, and the like), stored, and/or transported. As shown, hydrogenolysis product stream 116 exits reactor 102 via product outlet 108 and enters separation unit 118. In separation unit, 118, hydrogenolysis products (e.g., ethane, propane, methane or mixtures thereof) can be separated from unreacted butane and unreacted hydrogen. Unreacted hydrogen stream 120 can be recycled to hydrogen feed stream 112. Unreacted butane stream 122 can be recycled to butane feed stream 114. If the butane feed stream includes isobutane, the unreacted mixed butane stream can have a low n-butane/ isobutane (n/i) ratio. For example, the n/i ratio can be less than 1. In separation unit 118, unreacted iso-butane 124 can be separated from n-butane stream 122. Iso-butane stream 124 can exit separation unit 118 and enter isomerization unit 126. In isomerization unit 126, the isobutane can be converted to produce another mixed butane stream (enriched butane stream) having a n/i ratio of 1 or more. Enriched butane stream 128 can exit isomerization unit 126 and be combined with butane streams 114 and/or 122 to continue the process. As shown, the butane streams are all combined, however, butane stream 122 and butane stream 128 can each be independently fed to reactor 102.

Figure 2:
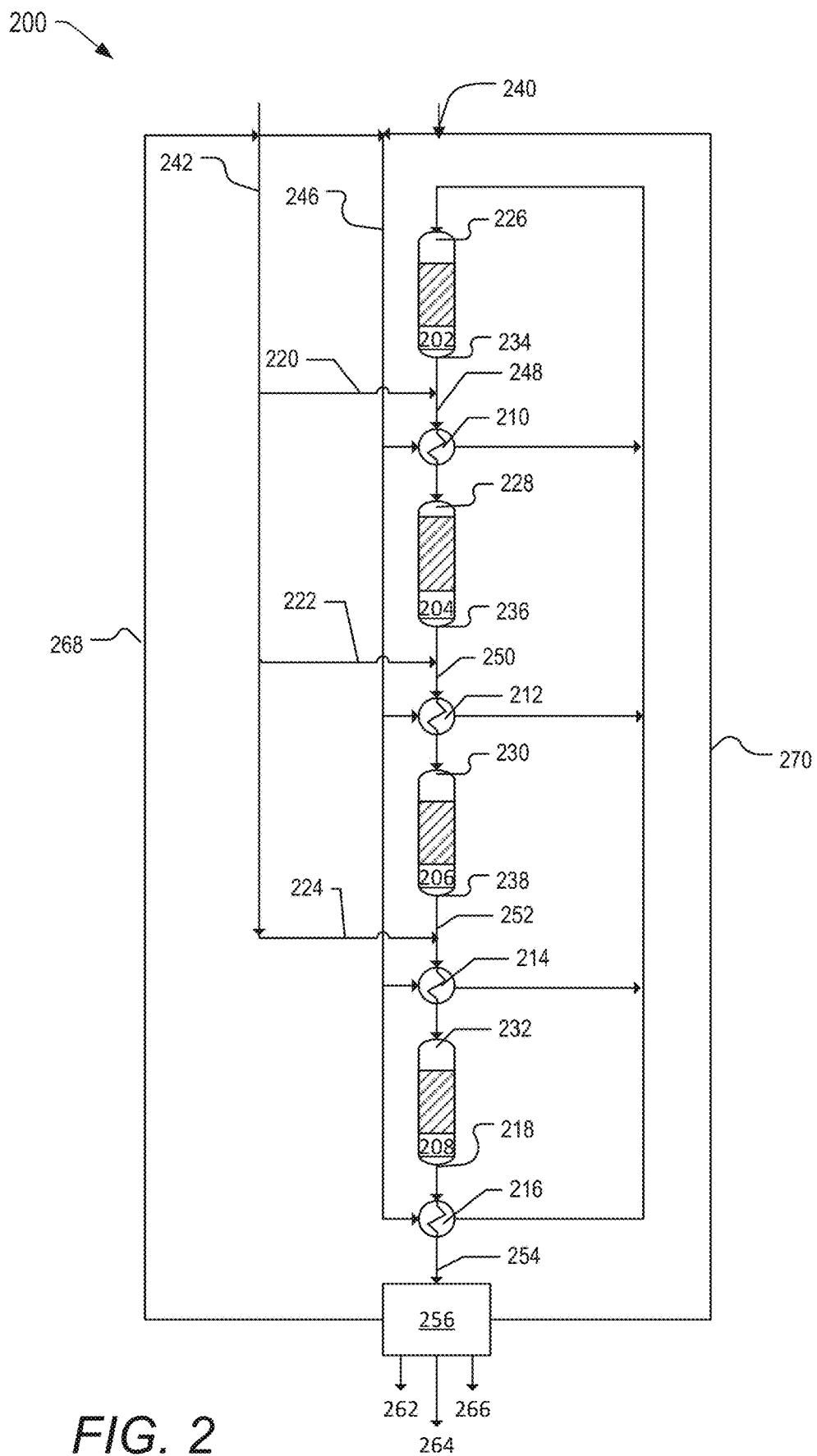
FIG. 2 is an illustration of sequential fixed bed reactors for the hydrogenolysis of butane.
Figure 3:
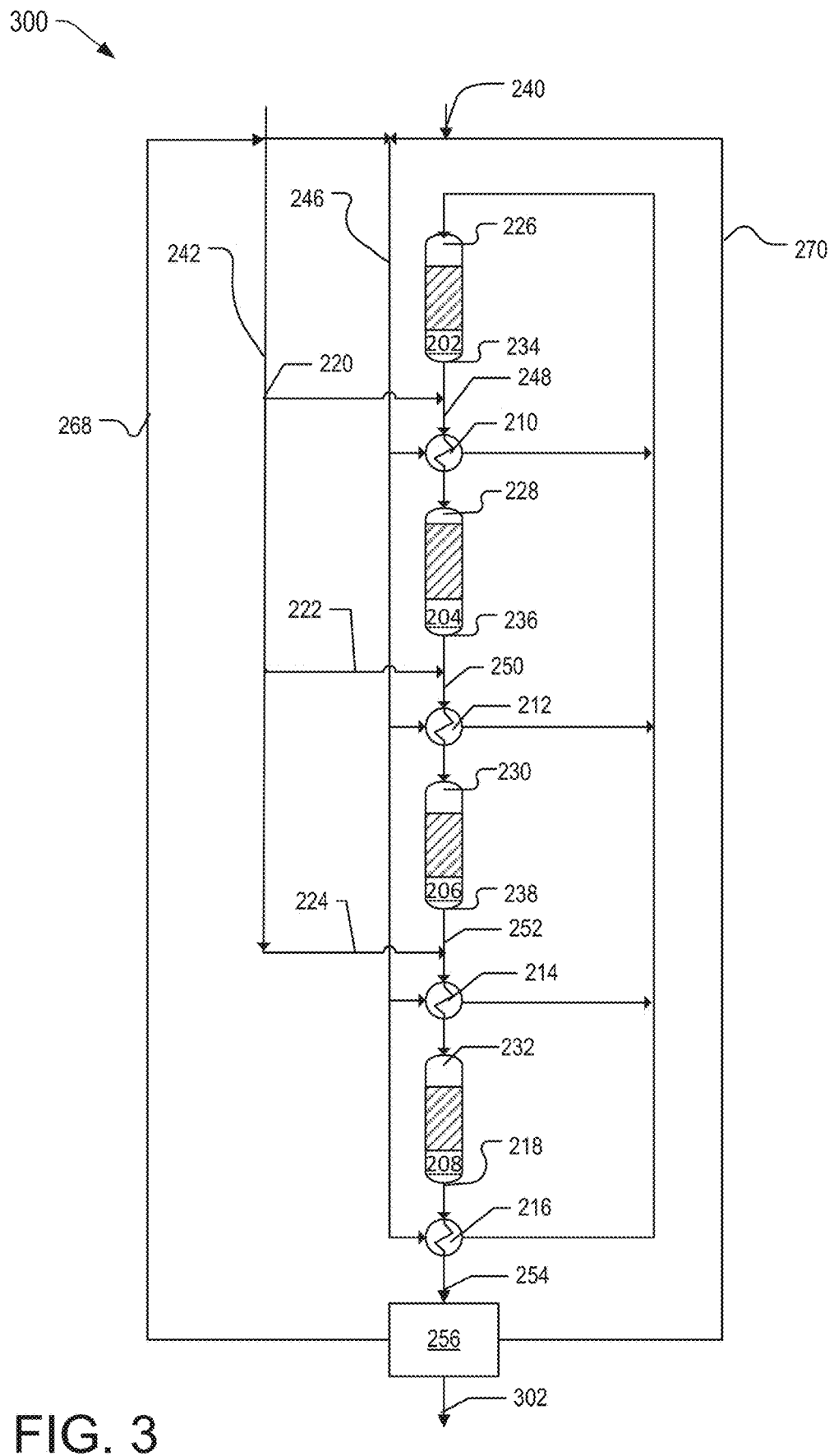
FIG. 3 is an illustration of sequential fixed bed reactors for a hydrogenolysis feed stream that include a mixture of n-butane and isobutane where isobutane is separated.
Figure 4:
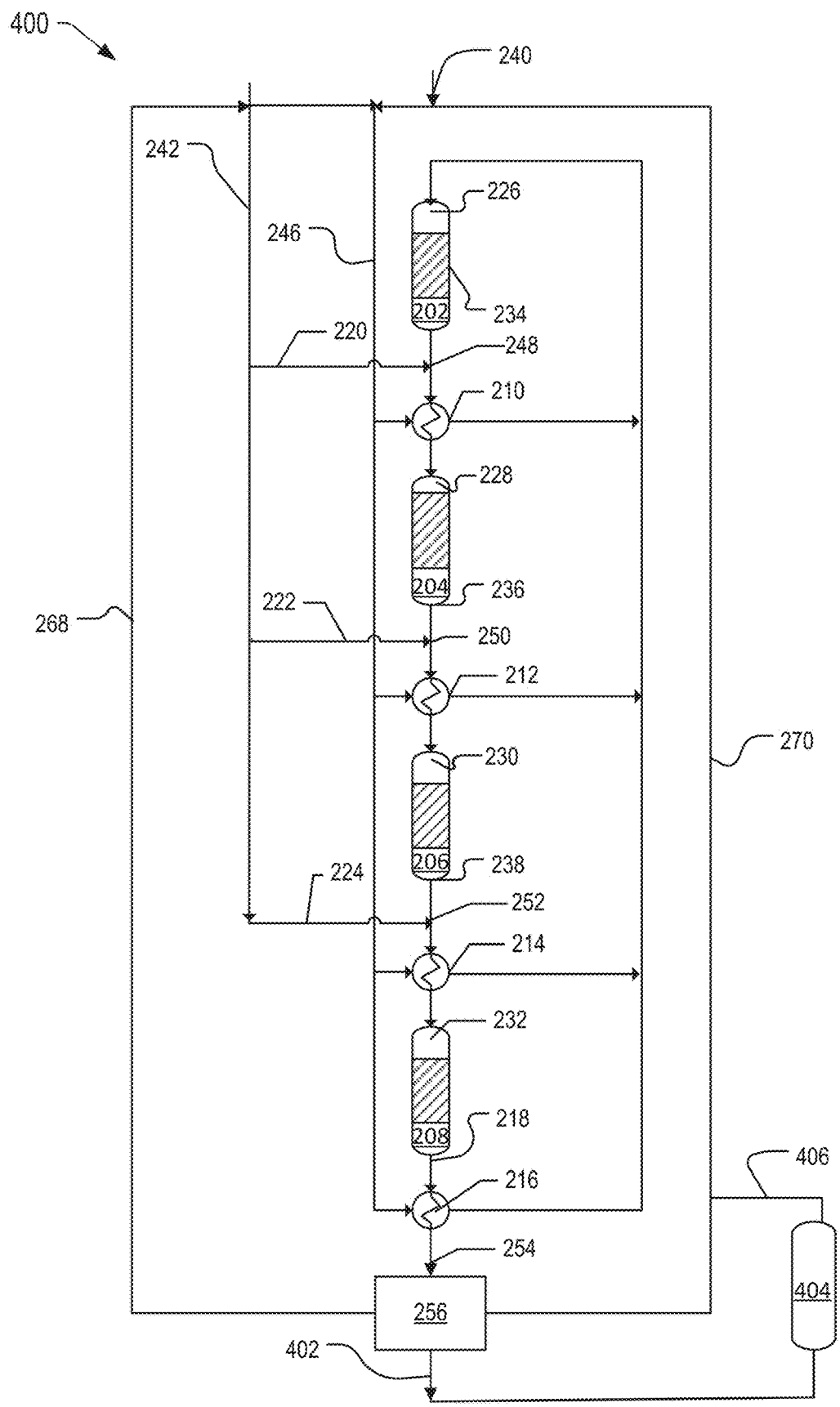
FIG. 4 is an illustration of sequential fixed bed reactors for a hydrogenolysis feed stream that include a mixture of n-butane and isobutane that includes separate recycling loops for n-butane and isobutane and an isomerization reactor in the isobutane recycling loop.
Figure 5:
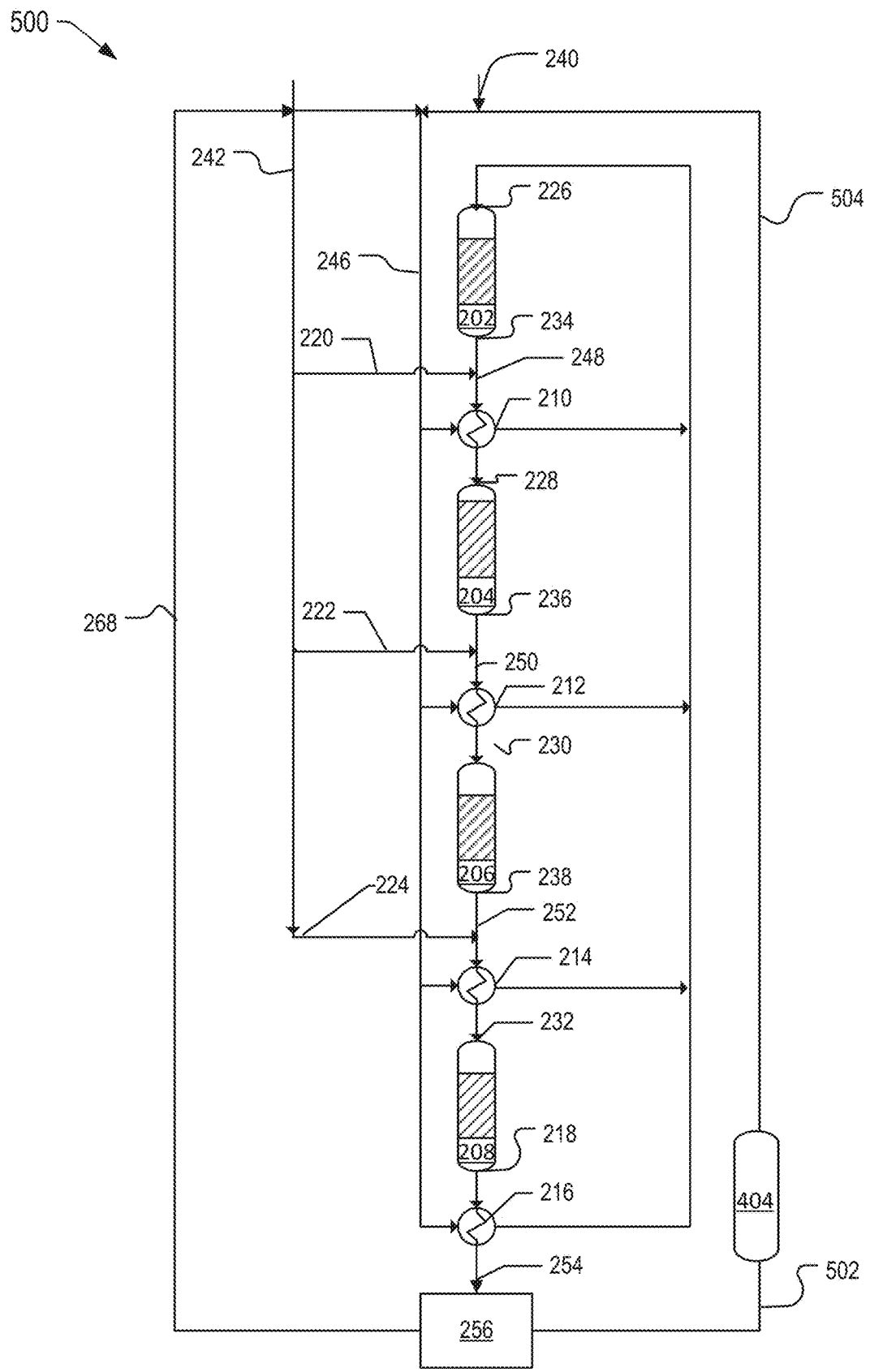
FIG. 5 is an illustration of sequential fixed bed reactors for a hydrogenolysis feed stream that include a mixture of n-butane and isobutane that includes a single recycling loop for n-butane and isobutane with an isomerization reactor.

Referring to FIGS. 2-5 schematics of sequential fixed bed reactors are illustrated. In FIG. 2 is an illustration of sequential fixed bed reactors for the hydrogenolysis of butane. FIG. 3 is an illustration of sequential fixed bed reactors for a hydrogenolysis feed stream that includes a mixture of n-butane and isobutane where isobutane is separated. FIG. 4 is an illustration of sequential fixed bed reactors for a hydrogenolysis feed stream that includes a mixture of n-butane and isobutane that includes a single recycling loop for n-butane and isobutane with an isomerization reactor. FIG. 5 is an illustration of sequential fixed bed reactor system using a mixed butane feed. The system includes separate recycling loops for n-butane and isobutane and an isomerization reactor in the isobutane recycling loop.

As shown in FIGS. 2-5, systems 200, 300, 400, and 500 include a number of sequential fixed bed reactors, 202, 204, 206, and 208. The number of reactors can be at least 2, preferably a range from 2 to 10, or 2, 3, 4, 5, 6, 7, 8, 9, or 10 reactors, or more. As shown in FIGS. 2-5, four reactors are used. The number of reactors used is within the skill of a person performing the reaction (e.g., an engineer or chemist). Heat exchangers 210, 212, 214, and 216 can be coupled to each reactor, preferably after each reactor so that the reaction exotherm can be used to pre-heat the feed before it enters the first reactor. The preferred direction of the sequential reactors is vertical, and the flow path in the reactors can be either upward or downward. Hydrogen gas can be injected at all reactors, but not into last reactor outlet 218. The injection points of $H_2$ can be either before or after heat exchanger 210, 212, 214, and 216 via $H_2$ conduits 220, 222, and 224, respectively. In some embodiments, the $H_2$ is injected after heat exchanges 210, 212, 214, and 216, or mixture of before and after. The inter-stage hydrogen can provide sufficient hydrogen to achieve butane conversion and ethane selectivity and to partially quench the reactor effluents.

The molar ratio of $H_2$ to $C_4H_{10}$ at the reactor inlet of any specific reactor (n) can be expressed as:

$$R_n = \frac{H_2 \text{ moles}}{C_4H_{10} \text{ moles}},$$

where n is the reactor number and R is the mole ratio.

The measurement of $H_2$ to $C_4H_{10}$ ratios can be direct (on-line GC analysis at the reactor inlet) or indirect (a combination of mass flowmeter readout and the kinetic model The measurement of $H_2$-to-$C_4H_{10}$ ratios in the reactor inlets (e.g., 202, 204, 206, and 208 inlets) can be determined by a person of engineering skill. For example, a direct on-line GC analysis in the reactor inlet(s) can be used to determine the $H_2/C_4H_{10}$ mole ratio in the $H_2/C_4H_{10}$ mixture. The in-line GC sample port is positioned downstream of the hydrogen and butane inlets, for example, but not limited to, in a middle section of the reactor inlet. In another example, mass flowmeters can be coupled to $H_2$ inlet(s) and $C_4H_{10}$ inlet(s) to regulate and/or monitor the amount of $H_2$ and $C_4H_{10}$ entering reactor inlet(s). The data from the mass flow meters can be used in combination with a kinetic model to determine the mole ratio of $H_2/C_4H_{10}$ in reactor inlet(s). The reactor number (n) can be any number in practical terms, n is preferably 10 or less, and more preferably 5 or less. Non-limiting values for n can be 1 to 10, or 1, 2, 3, 4, 5, 6, 7, 8, 9, or 10 or any range or value there between. At each reactor inlet 226 ($R_1$) 228 ($R_2$), 230 ($R_3$), 232 ($R_4$), it follows $R_1 \leq R_2 \leq R_3 \leq R_4$ and so on, where $C_4H_{10}$ includes both isobutane (if present) and n-butane. The value of $R_1$ is kept to no more than 0.8 to extend catalyst lifetime. Said another way, the amount of additional hydrogen injected (R) is selected such that a value of $R_1$ is less than 0.8, and the values of the hydrogen into sequential hydrogenolysis reactors ($R_{n+1}$) are such that $R_{n+1}$ is $\geq R_n$. In a preferred embodiment, $R_1$ is 0.3:1 to 0.8:1, or 0.3:1, 0.35:1, 0.4:1, 0.5:1, 0.55:1, 0.6:1, 0.65:1, 0.7:1, 0.75:1, 0.8:1 or any value or range there between. When $R_1$ is kept within this range the catalyst life is higher while maintaining the selectivity for ethane at greater than 50% (e.g., 50% to 95%) and the conversion of butane at least 50% (e.g., 50 to 95%). At reactor outlets 234, 236, 238, and 218, the ethane concentration and selectivity both increase as the reaction proceeds. For example, the ethane selectivity (SE) can be expressed a $SE_{234} < SE_{236} < SE_{238} < SE_{218}$. Said another way, the ethane selectivity at reactor outlet 218 can be greater than the ethane selectivity at reactor outlets 234, 236, and 238. As shown in a non-limiting manner in the Examples, ethane selectivity increased by 1% using the addition of hydrogen to the reactor as described.

Referring to FIG. 2, n-butane feed 240 and $H_2$ feed 242 enter a $H_2$/butane manifold to form $H_2$/butane feed stream 246. $H_2$/butane feed stream 246 can pass through heat exchanger 210 212, 214, or 216 and enter reactor inlet 226 of reactor 202. In reactor 202, contact of the $H_2$ and butane with a hydrogenolysis catalyst produces effluent stream 248 (first product stream). Effluent stream 248 exits reactor 202 via outlet 234, passes through heat exchanger 210 and enters reactor inlet 228 of reactor 204. $H_2$ feed 242 can be injected into reactor 204 via $H_2$ conduit 220 in amounts as described above. In reactor 204, contact of effluent stream 248 with $H_2$ added with a hydrogenolysis catalyst produces effluent stream 250 (second product stream), which is enriched in butane hydrogenolysis products as compared to effluent stream 248. Effluent stream 250 exits reactor 204 via outlet 236, passes through heat exchanger 212, and enters reactor inlet 230 of reactor 206. $H_2$ can be injected into reactor 206 or effluent stream 250 via $H_2$ conduit 224 in amounts as described above. In reactor 206, contact of effluent stream 250 and hydrogen with a hydrogenolysis catalyst produces effluent stream 252 (third product stream), which is enriched in butane hydrogenolysis products as compared to effluent streams 248 and 250. Effluent stream 252 exits reactor 206 via outlet 238, passes through heat exchanger 214 and enters reactor inlet 232 of reactor 208. Reactor 208 in FIG. 2 is the last reactor so no $H_2$ is injected into the reactor or the effluent stream. In reactor 208, contact of effluent stream 252 and hydrogen with a hydrogenolysis catalyst produces effluent stream 254 (fourth product stream), which is enriched in butane hydrogenolysis products as compared to effluent streams 248, 250, and 252. Effluent stream 254 (fourth product stream) exits reactor 208 via outlet 218, passes through heat exchanger 216, and enters separation unit 256. In separation unit 256, effluent stream 254 (or the last effluent stream when more than 4 reactors are used) can be separated into individual products streams (e.g., methane stream 262, ethane stream 264, and propane stream 266), unreacted $H_2$ and unreacted butane. Separation unit 256 can be a collection of known separation units. For example, separation unit 256 can include distillation units, membrane units, and the like. The type, number, and/or size of separation units to be used can be modified as desired (e.g., from a person of ordinary skill in the art). Unreacted $H_2$ can be recycled directly to the $H_2$ feed 242 via conduit 268. Unreacted n-butane stream 270 can be recycled directly to n-butane feed stream 240. Produced methane can be used as a fuel for the system or can be reacted with steam to make hydrogen. Produced ethane can be sent to other processing units, for example sent to a steam cracker to produce ethylene. Produced propane can be sent to other processing units, for example, sent to a cracking unit together with ethane or used for on-purpose propylene production through propane dehydrogenation.

Referring to FIG. 3, the process and system are the same as for FIG. 2 with the exception that the butane feed includes a mixture of n-butane and isobutane. In system 300, effluent stream 254 (fourth product stream) exits reactor 208 via outlet 218, passes through heat exchanger 216 and enters separation unit 256. In separation unit 256, the effluent stream (or the last effluent stream when more than 4 reactors are used) can be separated into individual products (e.g., methane, ethane, and propane), unreacted $H_2$, unreacted butane, and unreacted isobutane. Unreacted $H_2$ 268 can be recycled directly to the $H_2$ feed stream 242. Unreacted n-butane stream 270 can be recycled directly to the n-butane feed stream 240. Unreacted isobutane 302 can be sent to other processing units such as a methyl tertiary-butyl ether (MTBE) unit. Methane stream (not shown), propane stream (not shown), and ethane stream (not shown) can be stored and/or used as described above.

Referring to FIG. 4, the process and system are the same as for FIG. 3 with the exception that the unreacted isobutane stream is further processed. In system 400, unreacted isobutane stream 402 can be provided to isomerization unit 404. In isomerization unit 404, isobutane can be converted to n-butane using known isomerization methodology. Mixed butane stream 406 having a n/i ratio of about 1 can exit isomerization unit 404 and be combined with butane feed 270 to continue the cycle. Methane, propane, and butane can be stored and/or used as described above.

Referring to FIG. 5, the process and system are the same as for FIG. 3 with the exception that the unreacted mixed butane stream is not separated in separation unit 256, but processed as one stream. The unreacted mixed butane stream can have a low n-butane/isobutane (n/i) ratio. For example, the n/i ratio can be less than 1. In system 500, unreacted mixed butanes stream 502 can enter isomerization unit 404. In isomerization unit 404, isobutane in the mixed butane stream can be converted to n-butane using known isomerization methodology. Enriched n-butane stream 504 having a n/i ratio of about 1 can exit isomerization unit 404 and be combined with butane feed stream 240 to continue the cycle. Methane, propane, and butane can be stored and/or used as described above.

The temperature and pressure in reactors (e.g., reactors 202, 204, 206 and 208 in FIGS. 1-5) can be varied to maintain the temperature, conversion and selectivity of the inventive process and is within the skill of a person performing the reaction (e.g., an engineer or chemist). The flow of butane (e.g., and butane WHSV) and hydrogen to the hydrogenolysis reactor can be controlled (e.g., flow meters, valves, and the like) to maintain a hydrogen to butane molar ratio in the first reactor below 1, preferably between 0.3:1 and 0.8:1, or about 0.3:1, 0.35:1, 0.4:1, 0.45:1, 0.5:1, 0.55:1. 0.60:1, 0.65:1, 0.70:1, 0.75:1, 0.80:1, or any range or value there between. The butane feed stream can include a mixture of butanes (e.g., n-butane and isobutane) and minimal amounts of other hydrocarbons. The n-butane can be present in a mixed butane feed stream in an amount of equal to or greater than about 50 mol %. For example, the amount of n-butane can be equal to or greater than 50 mol. %, 55 mol. %, 60 mol. %, 65 mol. %, 70 mol. %, 75 mol. %, 80 mol. %, 85 mol. %, 90 mol. %, 95 mol. %, 99.9 mol. % or any range or value there between. In some embodiments, the amount of n-butane can be 50 mol. % to 99 mol. %, 55 mol. % to 90 mol. %, 60 mol % to 85 mol. %, 65 mol. % to 80 mol. %, or 70 mol. % to 75 mol. % or any range there between. Reactor conditions of the present invention can include temperature, pressure, a butane based WHSV, or combinations thereof. Temperature at the reactor(s) inlet(s) can range from 200° C. to about 350° C., 210° C. to 320° C., 220° C. to 310° C., 230° C. to 300° C., 240° C. to 290° C., 250° C. to 280° C., 260° C. to 270° C. or 200° C., 210° C., 220° C., 230° C., 240° C., 250° C., 260° C., 270° C., 280° C., 290° C., 300° C., 310° C., 320° C., 330° C., 340° C., or 350° C. or any value or range there between. When a series of reactors are used, the reactor(s) inlet(s) temperatures of each reactor can range from 240° C. to about 300° C., 245° C. to 290° C., 250° C. to 285° C., 260° C. to 280° C., or any value or range there between. In a preferred embodiment, the reactor inlet temperature of each reactor in a series of reactors is 245° C. to 290° C. In some embodiments, a temperature differential between the reactor inlet and reactor outlet of the reactor(s) can be maintained at 20° C. to 30° C., or 21° C., 22° C., 23° C., 24° C., 25° C., 26° C., 27° C., 28° C., 29° C., 30° C., or any range or value there between. In some aspects, the temperature differential between reactors is 35° C. to 45° C., or 35° C., 36° C., 37° C., 38° C., 39° C., 40° C., or any value or range there between. In some embodiments, reactor inlet temperatures can range from 240° C. to about 300° C., 245° C. to 290° C., 250° C. to 285° C., 260° C. to 280° C., or any value or range there between while maintaining a temperature differential between the reactor inlet and reactor outlet of the reactor(s) of 20° C. to 30° C., or 21° C., 22° C., 23° C., 24° C., 25° C., 26° C., 27° C., 28° C., 29° C., 30° C., or any range or value there between. Pressures can range from about 101 kPa (0 psig) to 2100 kPa (300 psig), 200 to 1500 kPa, 500 to 1000 kPa, or any range or value there between. Butane feed-based WHSV can range from about 1 $h^{-1}$ to about 100 $h^{-1}$, 1 $h^{-1}$, 2 $h^{-1}$, 3 $h^{-1}$, 4 $h^{-1}$, 5 $h^{-1}$, 6 $h^{-1}$, 7 $h^{-1}$, 8 $h^{-1}$, 9 $h^{-1}$, 10 $h^{-1}$, 20 $h^{-1}$, 21 $h^{-1}$, 22 $h^{-1}$, 23 $h^{-1}$, 24 $h^{-1}$, 25 $h^{-1}$, 26 $h^{-1}$, 27 $h^{-1}$, 28 $h^{-1}$, 29 $h^{-1}$, 30 $h^{-1}$, 35 $h^{-1}$, 40 $h^{-1}$, 45 $h^{-1}$, 50 $h^{-1}$, 60 $h^{-1}$, 65 $h^{-1}$, 70 $h^{-1}$, 75 $h^{-1}$, 80 $h^{-1}$, 85 $h^{-1}$, 90 $h^{-1}$, 95 $h^{-1}$, or 100 $h^{-1}$, or any range or value there between. In some embodiments, the butane based WHSV can be 5 $h^{-1}$ to 50 $h^{-1}$ with respect to the first reactor; and a butane-based WHSV of 1 $h^{-1}$ to 10 $h^{-1}$ with respect to the entire reactor series.

The reactor (e.g., reactors 102, 202, 204, 206, 208, etc.) can include one or more heating and/or cooling devices (e.g., insulation, electrical heaters, jacketed heat exchangers in the wall) or controllers (e.g., computers, flow valves, automated values, etc.) that can be used to control the reaction temperature and pressure of the reaction mixture. While only one reactor is shown, it should be understood that multiple reactors can be housed in one unit or a plurality of reactors housed in one heat transfer unit.

B. Catalysts

The hydrogenolysis catalyst used in the reactor systems 100 to 500 can be a bimetallic supported catalyst or a monometallic supported catalyst, or a mixture thereof. For example, reactors 102, 202, 204, 206, and 208 can each individual include a bimetallic catalyst and a monometallic catalyst. In some embodiments, one reactor can include a bimetallic catalyst and different reactor can include a monometallic catalyst. One of skilled in hydrogenolysis reactions (e.g., engineer and/or chemist) can determine the optimal order of catalysts in each reactor. The bimetallic supported catalyst can include two different catalytic metals (first and second catalytic metals), a support, and an optional binder. The monometallic supported catalyst can include a catalytic metal (third catalytic metal), that is different or the same as one of the catalytic metals of the bimetallic catalyst, a support and an optional binder. Catalytic metals can include iridium (Ir), platinum (Pt), rhodium (Rh), ruthenium (Ru), rhenium (Re), palladium (Pd), molybdenum (Mo), tungsten (W), nickel (Ni), or cobalt (Co), or a combination thereof.

The support can include alumina, a zeolite, or both. A non-limiting example of alumina is gamma alumina ($\gamma$-$Al_2O_3$). Non-limiting examples of zeolites include ZSM-5, ZSM-11, Y, high-silica Y, USY, EU-1, EU-2, beta, L, ferrierite, CHA, SSZ-16, Nu-3, sigma-1, silicalite-1, or combinations thereof. The zeolite can have $SiO_2/Al_2O_3$ of 250 to 300, or 250, 255, 260, 265, 270, 275, 280, 285, 290, 295 or 300. Non-limiting examples of a binder includes alumina, titania, silica, or combinations thereof.

The supported catalyst of the present invention can include up to 1 wt. % of the total amount of catalytic metal, from 0.1 wt. % to 1 wt. %, or from 0.3 wt. % to 0.7 wt. % and all wt. % there between including 0.3 wt. %, 0.35 wt. % 0.4 wt. %, 0.45 wt. %, 0.5 wt. %, 0.55 wt. %, 0.6 wt. %, 0.65 wt. %, and 0.7 wt. %. In a specific embodiment the supported catalyst includes about 0.6 wt. % of total catalytic metal.

Non-limiting examples of a bimetallic hydrogenolysis catalyst include Pt and Ir catalytic metals on a support. For example, the hydrogenolysis catalyst can include 0.3 wt. % Pt and 0.3 wt. % Ir/$\gamma$-$Al_2O_3$-HZSM-5. The support can include 80 wt. % H-ZSM-5 ($SiO_2/Al_2O_3$ of 280) and 20 wt. % $\gamma$-$Al_2O_3$.

EXAMPLES

The present invention will be described in greater detail by way of specific examples. The following examples are offered for illustrative purposes only, and are not intended to limit the invention in any manner. Those of skill in the art will readily recognize a variety of noncritical parameters which can be changed or modified to yield essentially the same results.

General Procedure: Hydrogenolysis of Butane-Single Pass Reactor and Lean Hydrogen Experiments were performed to demonstrate the advantage of operating hydrogenolysis of butanes under hydrogen-lean conditions. Mixed butane (70% n-butane+30% isobutane) was used as feed. The catalyst was prepared according to International Patent Application Publication No. WO 2020/061012 to Dasari et al. The catalyst composition was 0.3 wt. % Pt-0.3 wt. % Ir/$\gamma$-$Al_2O_3$-HZSM-5. The catalyst carrier was composed of 80 wt. % H-ZSM-5 and 20 wt. % $\gamma$-$Al_2O_3$. The H-ZSM-5 had a $SiO_2/Al_2O_3$ of 280.

All the experiments were conducted in differential reactors. All the $H_2/C_4H_{10}$ ratios specified below are molar. Within a reasonably wide range of process conditions (Pressure: 50 to 200 psig, Temperature: 250° C. to 325° C.), the optimal catalyst lifetime was found to be a $H_2$ to $C_4H_{10}$ molar ratio between 0.3:1 and 0.8:1, preferably 0.5:1 to 0.8:1, most preferably 0.7:1 to 0.8:1. The single-pass conversion for $C_4H_{10}$ or $H_2$ was below 30%, and the unconverted $H_2$ and $C_4H_{10}$ was either recycled to the reactor, or sent to sequential reactors for higher conversion.

Example 1

Hydrogenolysis of Butane-Catalyst Activity-Single Pass Reactor Comparative Vs. Invention Mole Ratio at 275° C.

Figure 6:
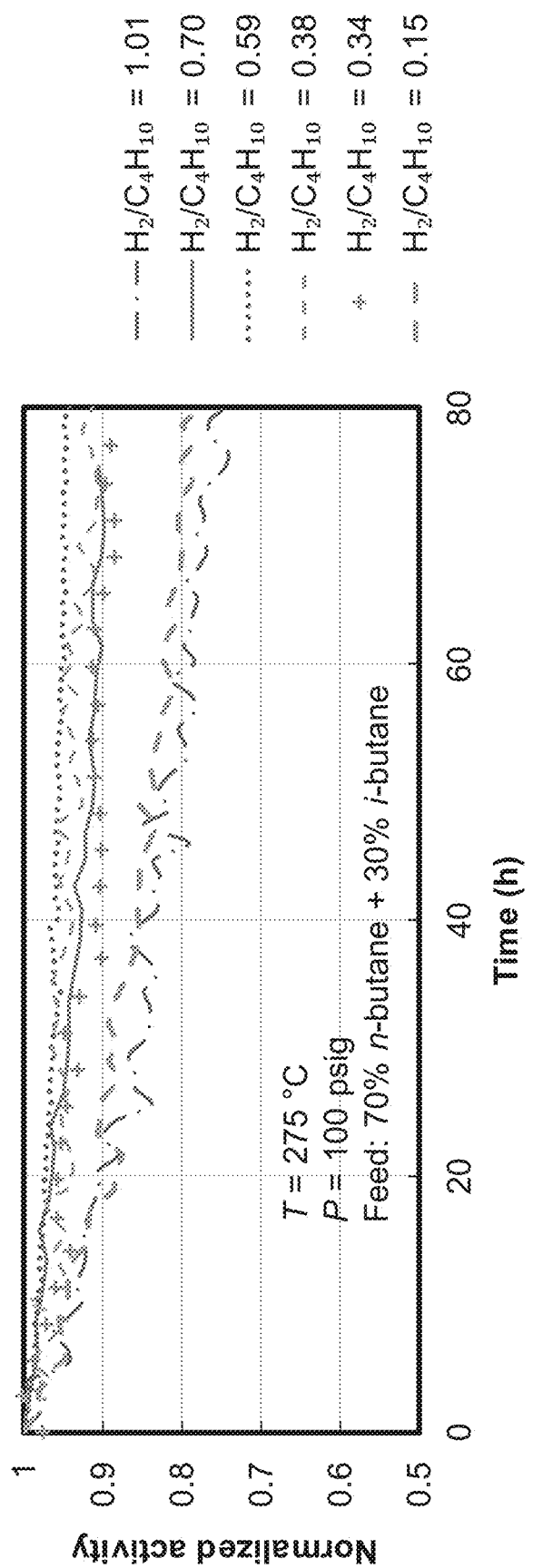
FIG. 6 show deactivation profiles of a support Pt—Ir catalyst in a butane hydrogenolysis reaction under 275° C. and 100 psig (about 690 kPa) using a butane mixture (70% n-butane+30% isobutane) as the feed. The catalyst being 0.3 wt. % Pt-0.3 wt. % Ir on a support including 20 wt. % γ-$Al_2O_3$ and 80 wt. % H-ZSM-5.

Using the single pass reactor and catalyst described in the General Procedure section above, the catalyst activity was measured at various $H_2/C_4H_{10}$ ratios at a temperature of 275° C. and a pressure of 100 psig, and WHSVs as shown in Table 1. The results are illustrated in FIG. 6 and tabulated in Table 1. In this figure, steeper slope indicated faster catalyst deactivation (short catalyst lifetime), and vice versa. When the $H_2/C_4H_{10}$ was between 0.34 at 23 $h^{-1}$ and 0.70 at 32 $h^{-1}$, catalyst deactivation was the most minimized. After 80 h on stream, the catalyst activity at the $H_2/C_4H_{10}$ molar ratio of 0.59 at 14 $h^{-1}$ dropped less than 10%, which was significantly less than the activity drop at the $H_2/C_4H_{10}$ ratios of 0.15 and 1.01. Notably, when the $H_2/C_4H_{10}$ ratio was less than 0.34 and greater than 1.01, the catalyst deactivated faster than that at the $H_2/C_4H_{10}$ ratio from 0.34 to 0.7. Thus The $H_2/C_4H_{10}$ molar ratio that had the slowest deactivation at given conditions (T=275° C., P=100 psig) was between the critical values of 0.3 and 0.80.

TABLE 1

| $H_2/C_4H_{10}$ | WHSV ($h^{-1}$, $C_4H_{10}$-based) | Initial n-$C_4H_{10}$ conversion |
| --- | --- | --- |
| 1.01 | 20 | 23% |
| 0.70 | 32 | 12% |
| 0.59 | 14 | 20% |
| 0.38 | 39 | 6.0% |
| 0.34 | 23 | 12% |
| 0.15 | 54 | 4.4% |

Example 2

Hydrogenolysis of Butane-Catalyst Activity-Single Pass Reactor Comparative Vs. Invention Mole Ratios at 310° C.

Figure 7:
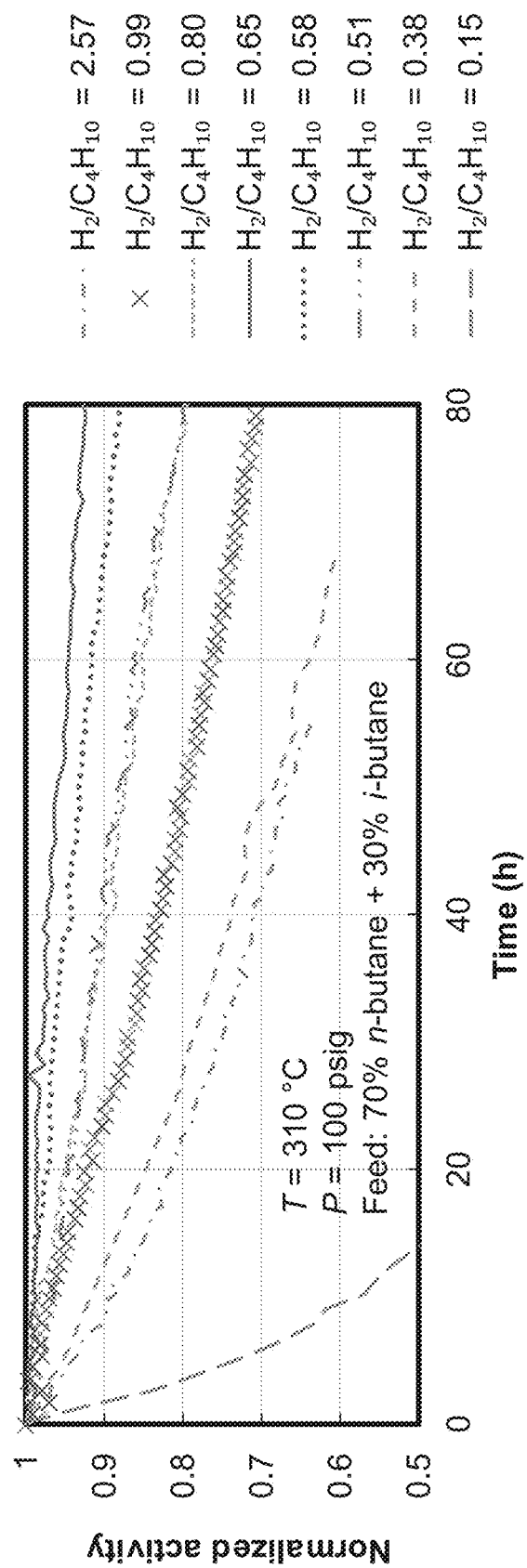
FIG. 7 show deactivation profiles of supported Pt—Ir catalyst in a butane hydrogenolysis reaction under 310° C. and 100 psig (about 690 kPa). The catalyst being 0.3 wt. % Pt-0.3 wt. % Ir on a support including 20 wt. % γ-$Al_2O_3$ and 80 wt. % H-ZSM-5.

Using the single pass reactor and catalyst described in the General Procedure section above, the catalyst activity was measured at various $H_2/C_4H_{10}$ ratios at a temperature of 310° C. and 100 psig. The results are illustrated in FIG. 7 and tabulated in Table 2. The deactivation rates were observed at the $H_2/C_4H_{10}$ molar ratios of the present invention at about 0.3:1 to 0.8:1, with the slowest rates being at 0.5:1 to 0.8:1 molar ratios. In a comparative example, when the $H_2/C_4H_{10}$ molar ratio decreased further below 0.3, the catalyst deactivation become faster than at $H_2/C_4H_{10}$ of about 0.15:1. In other comparative examples, when the $H_2/C_4H_{10}$ ratio increased from greater than 0.8:1 to 2.57:1, under the same conditions, catalyst deactivation rate accelerated.

TABLE 2

| $H_2/C_4H_{10}$ | WHSV (h$^{-1}$, C$_4$H$_{10}$-based) | Initial n-C$_4$H$_{10}$ conversion |
|---|---|---|
| 2.57 | 49 | 33% |
| 0.99 | 62 | 22% |
| 0.80 | 88 | 18% |
| 0.65 | 74 | 14% |
| 0.58 | 112 | 5.6% |
| 0.51 | 126 | 4.2% |
| 0.38 | 105 | 3.5% |
| 0.15 | 171 | 0.9% |

Example 3

Reaction Rate—Single Pass Reactor

Figures 8A, 8B:
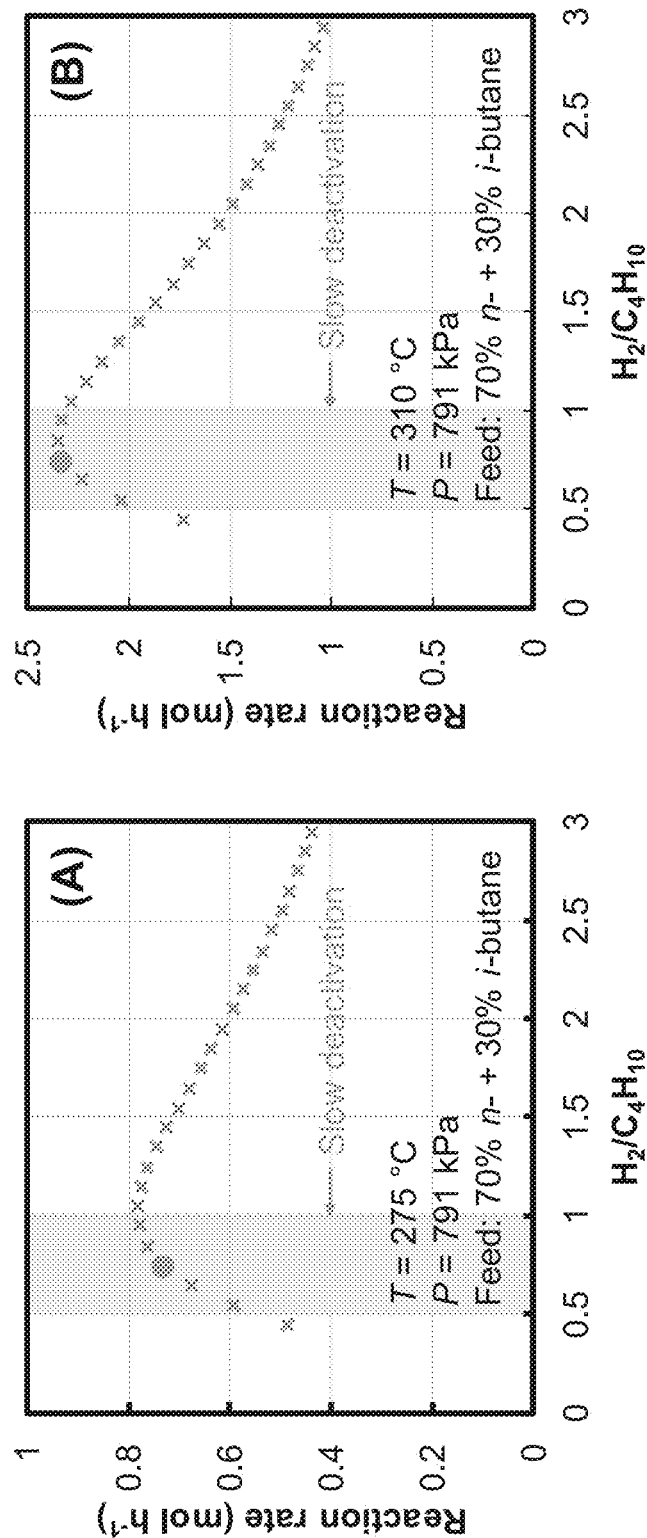
FIGS. 8A and 8B show the evolution of reaction rate as a function of $H_2/C_4H_{10}$ ($C_4H_{10}$: 70% n-butane+30% isobutane) at 100 psig (about 690 kPa), (6A) 275° C. and (6B) 310° C. Plotted with a kinetic model developed using experimental data in lab reactors. The shaded areas represent the slow-deactivation conditions shown in Examples 1 and 2.

From Examples 1 and 2, the slow-deactivation conditions could overlap with those with fast reaction rates. As shown in FIG. 8, the maximum reaction rate (scaled linearly on the vertical axis) appeared at the region where the $H_2/C_4H_{10}$ was between 0.75 and 1.5. In combination of the slow-deactivation conditions presented in Examples 1 and 2 (shaded areas in FIG. 8), the catalyst offered relatively high activity and slow deactivation at $H_2/C_4H_{10}$ molar ratio of 0.75:1 to 0.8:1.

Example 4

Hydrogenolysis of Butane-Sequential Reactors and Inter-Stage Hydrogen—Hydrogen Injection A mixture of butanes (typical composition: 70% n-butane+30% isobutane, which may vary) was used as the hydrocarbon reactant. The catalyst was a 0.3 wt. % Pt-0.3 wt. % Ir/γ-Al$_2$O$_3$-HZSM-5 and prepared according to International Patent Application Publication No. WO 2020/061012 to Dasari et al. The catalyst carrier was composed of 80 wt. % H-ZSM-5 and 20 wt. % γ-Al$_2$O$_3$. The H-ZSM-5 had a SiO$_2$/Al$_2$O$_3$ of 280.

FIGS. 9A-9E and 10A-B illustrate four cases that demonstrated the advantages of inter-stage hydrogen injection, using a four-reactor example to resemble the configuration in FIGS. 2-5. The plots were made based on models of reaction kinetics and catalyst deactivation, both of which were developed in-house using experimental data.

Case 1 corresponded to the present invention with a $H_2/C_4H_{10}$ molar ratio of 0.75 at the head (reactor inlet) of the first reactor (e.g., 202) without inter-stage H$_2$ injection. Case 2 corresponded to the present invention with a $H_2/C_4H_{10}$ molar ratio of 0.75 in the first reactor and with the incremental inter-stage H$_2$ injection at each reactor inlet. The inter-stage hydrogen injection follows R$_1$ (0.75)≤R$_2$ (1)≤R$_3$ (1.5)≤R$_4$ (2.25) as discussed in the specification, in which 226, 228, 230, and 232 refer to the reactor inlets in which hydrogen is injected. Case 3 corresponded to a comparative experiment where the $H_2/C_4H_{10}$ molar ratio was 1.74 without inter-stage injection. In Case 3, the total amount of H$_2$ added to the first reactor was the same as the sum of the amounts added in Case 2. The data represents the conditions and catalyst performances after 1000 hours on stream.

The reactor inlet temperatures of each reactor were between 240° C. and 325° C. and were chosen to maintain the temperature rise in each reactor to be 40° C. At this temperature rise in each reactor, butane conversion of around 20% was achieved. At the outlet of the last reactor, n-butane conversion was higher than 50%, while that of isobutane (if present in the feed) was below 15%.

Figures 9A, 9B, 9C, 9D, 9E:
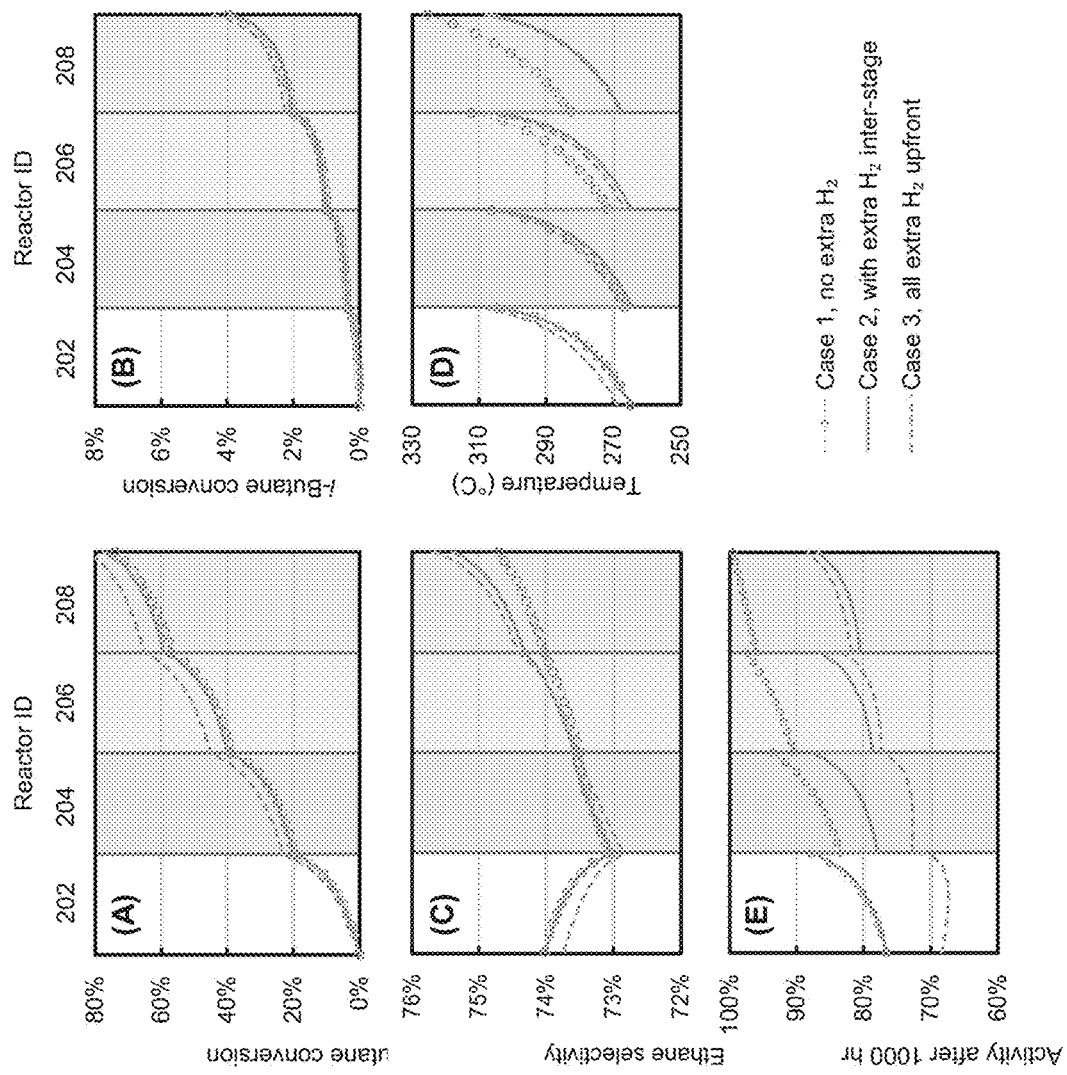
FIGS. 9A-9E are illustrations of three cases to demonstrate performance in four sequential adiabatic reactors.

As the results show, sequencing reactors benefited all three cases such that n-butane conversion increased gradually from 20% to above 70% (FIG. 9A) with limited isobutane conversion below 5% (FIG. 9B). Since the conversion of isobutane gave worse ethane selectivity than n-butane and it had to be limited.

Regardless of inter-stage (Case 2, present invention) or all upfront (Case 3, comparative), the extra hydrogen resulted in about 1% higher ethane selectivity (FIG. 9C) than Case 1 (low $H_2/C_4H_{10}$ entering the Reactor 202 and no inter-stage hydrogen, present invention), showed that the extra H$_2$ improved ethane selectivity. Case 2 and Case 3 had similar temperature profiles across the all reactors and required lower temperatures in reactors 204, 206 and 208 than Case 1 (FIG. 9D).

The catalyst lifetime largely depended on the reaction conditions (temperature, concentration of reactants, etc.). The catalyst lifetime was quantified in terms of the variation of activity with time (FIG. 9E). The initial activity was defined as 100%, which represented fresh catalyst in all reactors. After 1000 hours of reactor operation, the first reactor (202) showed the fastest deactivation (FIG. 9E) as compared to the other reactors in all three cases. Case 1 and Case 2 (present invention) behaved similarly as they outperformed Case 3 (comparative) by a considerable margin. Although the catalyst activity was more stable in the second through fourth reactors (e.g., reactors 204, 206 and 208, FIGS. 2-5) in Case 1 (present invention) than the corresponding ones in Case 2 (present invention), it did not affect the lifetime of the entire catalyst load, which was governed by the first reactor (e.g., reactor 202, FIGS. 2-5) (where the most severe deactivation occurs). Therefore, from the catalyst stability perspective, Case 1 and Case 2 (present invention) were similar, and both were superior to Case 3 (comparative). Although Case 3 (comparative) generated about 1% higher ethane selectivity than Case 2 (FIG. 9C), the superior catalyst stability in Case 2 resulted in about 56% more ethane than Case 3 during the lifespan of the catalyst.

Example 5

Figures 10A, 10B:
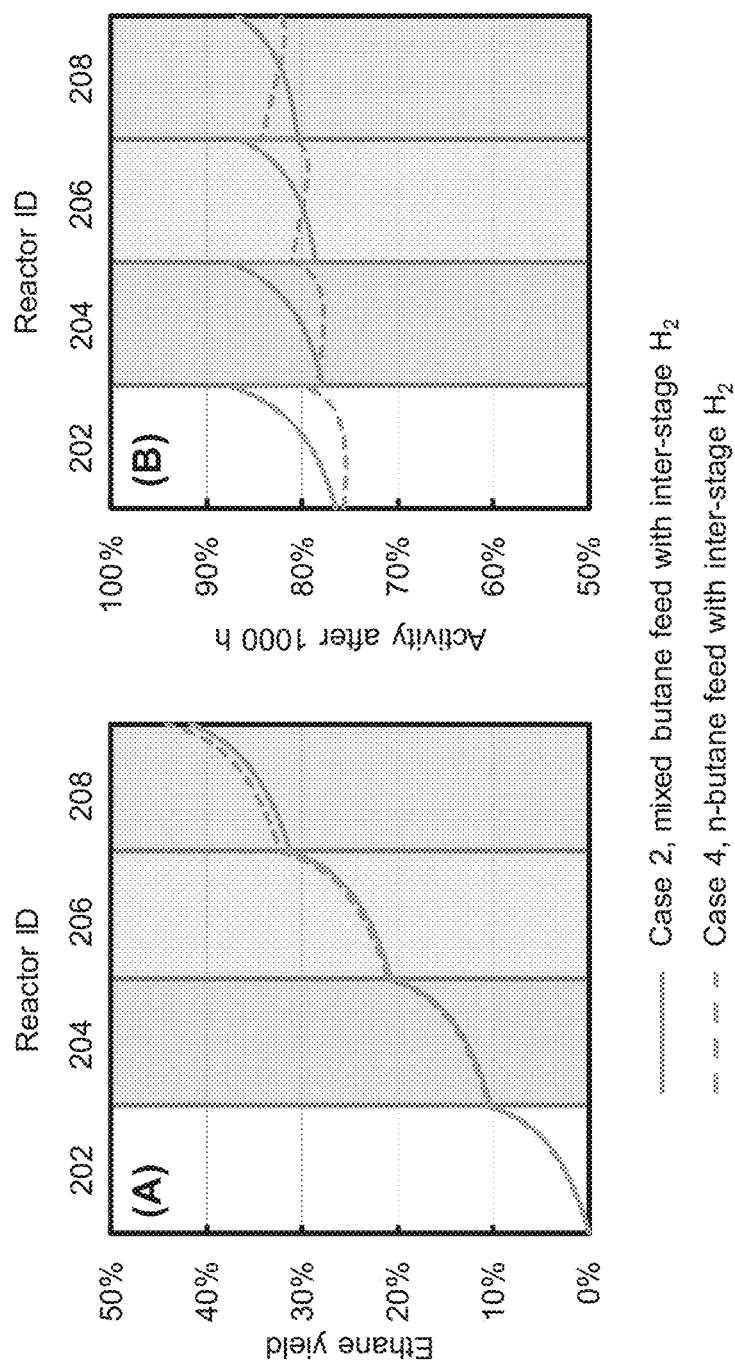
FIGS. 10A and 10B are illustrations of the effect of the composition of the butane feed stream. Case 2 was extra $H_2$ via inter-stage addition for a butane feed of 70 wt. % n-butane and 30 wt. % isobutane. Case 4 is extra $H_2$ via inter-stage addition for 100% n-butane feed.

Hydrogenolysis of Butane-Sequential Reactors and Inter-Stage Hydrogen—Feed Selection Besides the inter-stage H$_2$ injection, the feed composition also played a role in catalyst deactivation. Using the conditions of Example 4, mixed butane feed and n-butane feeds were evaluated. FIGS. 10A and 10B are illustrations of the data for the performance of the butane hydrogenolysis reaction using butane mixture (Case 2, present invention, 70% n-butane and 30% isobutane) and n-butane (Case 4, present invention, same conditions as Case 2) as feeds. The two cases gave similar ethane yield (slightly above 40%) at the outlet of the fourth reactor (FIG. 10A). In FIG. 10B, the area between the 100% line and an activity curve after 100 h represented the percentage loss of activity from the fresh catalyst. The n-butane feed resulted in a 24% loss of activity in the first reactor while the butane mixture feed (70% n-butane+30% isobutane) caused a 20% loss. Case 2 is hence projected to have a catalyst lifetime 20% longer than Case 4.

From the data, it was determined that Case 1, Case 2 and Case 4 all provided superior results over Case 3 (comparative). Of the cases of the present invention, Case 2 which used mixed butane feed and inter-stage hydrogen injection, gave the best results to enhance ethane production and extend catalyst lifetime.

Example 6

Figure 11:
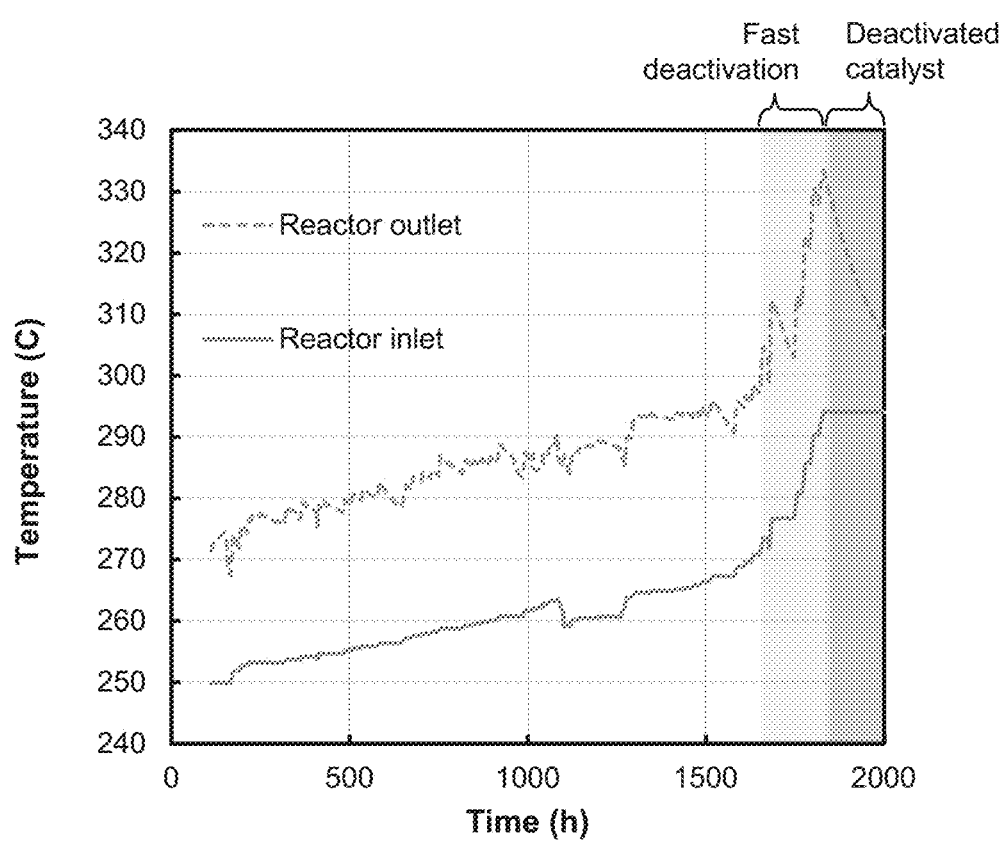
FIG. 11 is a graphical illustration of the reactor outlet (top line) and reactor inlet (bottom line) temperatures of a first reactor in a series of reactors of an 80-day trial to demonstrate performance in four sequential adiabatic reactors. Conditions: Reactor inlet temperature 245 to 290° C., WHSV=12 $h^{-1}$, catalyst: 0.3 wt. % Pt-0.3 wt. % Ir/γ-$Al_2O_3$—H-ZSM-5, ΔT=25° C. (of each reactor inlet and outlet).

Hydrogenolysis of Butane-Sequential Reactors and Inter-Stage Hydrogen—80 Day Trial Using the reactors and catalyst of Example 4, an eighty (80) day trial was conducted. The trial conditions are as follows: WHSV=12 h$^{-1}$, H$_2$ to C$_4$H$_{10}$ molar ratio: 1.2 up to 1050 hours and 0.75 from 1050 hours onwards. Inter-stage hydrogen injection was started at 1270 hours. Reactor inlet temperatures were adjusted during the trial to maintain a reactor ΔT (difference between the reactor outlet and reactor inlet temperature) of about 25° C. of all the reactors. Reactor inlet temperatures gradually increased over time to compensate for catalyst deactivation. Throughout the trial the temperature difference of 25° C. was maintained up to about 1750 hours (about 72 days) after which the catalyst was almost completely deactivated and large steps in inlet temperature were required to maintain some activity (see, bottom line). FIG. 11 shows the reactor inlet and reactor outlet temperatures of the first reactor of the 80-day adiabatic trial. As shown in FIG. 11, after changing the ratio from 1.2 to 0.75, the catalyst deactivation was slower, indicating by the lower rate of temperature increment (0.29° C./day at H$_2$/C$_4$H$_{10}$=1.2 vs. 0.076° C./day at H$_2$/C$_4$H$_{10}$=0.75).

Although embodiments of the present application and their advantages have been described in detail, it should be understood that various changes, substitutions and alterations can be made herein without departing from the spirit and scope of the embodiments as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the above disclosure, processes, machines, manufacture, compositions of matter, means, methods, or steps, presently existing or later to be developed that perform substantially the same function or achieve substantially the same result as the corresponding embodiments described herein can be utilized. Accordingly, the appended claims are intended to include within their scope such processes, machines, manufacture, compositions of matter, means, methods, or steps.

The invention claimed is:

1. A process for the hydrogenolysis of butane, the process comprising:
    (a) introducing a butane feed and hydrogen to a first hydrogenolysis reactor comprising a hydrogenolysis catalyst; and
    (b) contacting the butane feed and hydrogen with the hydrogenolysis catalyst at conditions sufficient to produce a hydrogenolysis product stream,
    (c) feeding the hydrogenolysis product stream to a separation unit to separate (i) an unreacted hydrogen stream, an unreacted n-butane stream, and an unreacted isobutane stream, or (ii) an unreacted hydrogen stream and an unreacted mixed butane stream comprising n-butane and isobutane,
    (d) feeding the unreacted isobutane stream or the unreacted mixed butane stream to an isomerization unit, and converting isobutane in the unreacted isobutane stream or the unreacted mixed butane stream to n-butane and produce an isomerized stream enriched in n-butane, and
    (e) recycling the unreacted hydrogen stream, the unreacted n-butane stream, if present, and the isomerized stream to the first hydrogenolysis reactor to increase conversion of the butane feed and hydrogen,
    wherein the introduction of the butane feed and hydrogen to the first hydrogenolysis reactor is controlled to effect a hydrogen to butane molar ratio in a reactor inlet of the first hydrogenolysis reactor of 0.3:1 to 0.8:1.

2. The process of claim 1, wherein the hydrogen to butane molar ratio in the reactor inlet is 0.5:1 to 0.8:1.

3. The process of claim 1, wherein the butane feed comprises n-butane and iso-butane and n-butane is present in the butane feed in an amount of equal to or greater than about 50 mol %.

4. The process of claim 1, wherein the conditions comprise a temperature of 245° C. to about 330° C., a pressure of from about 101 kPa (absolute) to about 2100 kPa (absolute), and a butane-based weight hourly space velocity (WHSV) of 1 h$^{-1}$ to about 100 h$^{-1}$.

5. The process of claim 1, wherein the hydrogenolysis catalyst comprises:
    (a) a bimetallic supported catalyst comprising a support, a first catalytic metal, a second catalytic metal, and optionally binder, wherein the first and second catalytic metals are different,
    (b) a monometallic supported catalyst, the monometallic catalyst comprising a third catalytic metal, a support, and optionally binder, or
    (c) mixtures of (a) and (b),
    wherein the first metal, the second metal, and the third metal each independently include iridium (Ir), platinum (Pt), rhodium (Rh), ruthenium (Ru), rhenium (Re), palladium (Pd), molybdenum (Mo), tungsten (W), nickel (Ni), or cobalt (Co), or any combination thereof.

6. The process of claim 5, wherein the hydrogenolysis catalyst comprises the bimetallic supported catalyst comprising Ir and Pt.

7. The process of claim 6, wherein the support comprises alumina, zeolite, or both, wherein the zeolite comprises ZSM-5 zeolite, ZSM-11 zeolite, zeolite Y, USY zeolite, EU-1 zeolite, EU-2 zeolite, zeolite beta, zeolite L, ferrierite zeolite, CHA zeolite, SSZ-16 zeolite, Nu-3 zeolite, sigma-1 zeolite, silicalite-1 zeolite, or any combination thereof, and wherein the optionally binder comprises alumina, titania, silica, or combination thereof.

8. The process of claim 7, wherein the hydrogenolysis catalyst comprises 0.3 wt. % Pt-0.3 wt. % Ir/γ-Al$_2$O$_3$-HZSM-5.

9. The process of claim 8, wherein the support is 80 wt. % H-ZSM-5 and 20 wt. % γ-Al$_2$O$_3$.

10. The process of claim 1, wherein the step of contacting the butane feed and hydrogen with the hydrogenolysis catalyst at conditions sufficient to produce a hydrogenolysis product stream comprises contacting the butane feed and hydrogen with the hydrogenolysis catalyst in the first hydrogenolysis reactor to produce a first hydrogenolysis product stream and feeding unconverted hydrogen and unconverted butane feed from the first hydrogenolysis product stream to one or more sequential hydrogenolysis reactors to increase overall conversion of the butane feed and produce the hydrogenolysis product stream.

11. The process of claim 1, wherein the step of contacting the butane feed and hydrogen with the hydrogenolysis catalyst at conditions sufficient to produce a hydrogenolysis product stream comprises contacting the butane feed and hydrogen with the hydrogenolysis catalyst in the first hydrogenolysis reactor to produce a first hydrogenolysis product stream and feeding the first hydrogenolysis product stream from the first hydrogenolysis reactor to one or more sequential hydrogenolysis reactors to form one or more sequential hydrogenolysis product streams to increase conversion of the butane feed, wherein the last stream of the one or more sequential hydrogenolysis product streams is the hydrogenolysis product stream.

12. The process of claim 11, further comprising passing the first hydrogenolysis product stream and any one or more of product streams from the one or more sequential hydrogenolysis reactors through a heat exchanger.

13. The process of claim 11, wherein the at a reactor inlet of the first hydrogenolysis reactor and/or of the one or more sequential hydrogenolysis reactors is between 240° C. and 300° C.

14. The process of claim 13, further comprising injecting additional hydrogen into the one or more sequential hydrogenolysis reactors.

15. The process of claim 14, further comprising selecting an amount of additional hydrogen based on $R_{n+1} \geq R_n$ where $R_n$ represents the molar ratio of hydrogen to butane in a reactor inlet of a $n^{th}$ reactor, and $R_{n+1}$ represents the molar ratio of hydrogen to butane in a reactor inlet of a $(n+1)^{th}$ reactor.

* * * * *

UNITED STATES PATENT AND TRADEMARK OFFICE
CERTIFICATE OF CORRECTION

| | | |
|---|---|---|
| PATENT NO. | : 11,254,628 B1 | |
| APPLICATION NO. | : 16/941031 | |
| DATED | : February 22, 2022 | |
| INVENTOR(S) | : Heng Shou et al. | |

It is certified that error appears in the above-identified patent and that said Letters Patent is hereby corrected as shown below:

In the Claims

On Column 19, Line 15 should read as follows:
13. The process of claim 11, wherein the temperature at a reactor inlet Signed and Sealed this
Thirtieth Day of August, 2022

Katherine Kelly Vidal
*Director of the United States Patent and Trademark Office*